United States Patent [19]

Alderete

[11] Patent Number: 4,707,442
[45] Date of Patent: Nov. 17, 1987

[54] **HYBRID CELL LINE PRODUCING MONOCLONAL ANTIBODY CYTOLYTIC TO *TRICHOMONAS VAGINALIS***

[75] Inventor: John F. Alderete, San Antonio, Tex.

[73] Assignee: Board of Regents, The University of Texas System, Austin, Tex.

[21] Appl. No.: 650,417

[22] Filed: Sep. 14, 1984

Related U.S. Application Data

[63] Continuation-in-part of Ser. No. 544,473, Oct. 24, 1983.

[51] Int. Cl.$^4$ .................. G01N 33/571; C12N 15/00; C12N 5/00; A61K 39/395
[52] U.S. Cl. .................................... 435/7; 435/172.2; 435/240.27; 435/948; 436/510; 436/548; 530/387; 530/808; 530/809; 935/103; 935/110; 935/107
[58] Field of Search ...................... 435/4, 7, 68, 172.2, 435/240, 948; 436/510, 548; 530/387, 808, 809; 935/103, 110, 107

[56] References Cited

PUBLICATIONS

Torian et al, Inf. Immun., 43(1):270–275, Jan. 1984.
Fridenberg (ed.), Basic & Clinical Immunology, 2nd edition, Lange Medical Publications, Los Altos, Calif., (1978), 372, 373, 690.
Kohler et al, Nature, 256, 495–497 (1975).
"Identification of Immunogenic and Antibody–Binding Membrane Proteins of Pathogenic *Trichomonas vaginalis*", John F. Alderete, *Infection and Immunity*, vol. 40(1), pp. 284–291 (Apr. 1983).
"Antigen Analysis of Several Pathogenic Strains of *Trichomonas vaginalis*", John F. Alderete, *Infection and Immunity*, vol. 39(3), pp. 1041–1047 (Mar. 1983).
"Enzyme Linked Immunosorbent Assay for Detecting Antibody to *Trichomonas vaginalis*", John F. Alderete, *British Journal of Venereal Diseases*, vol. 60, pp. 164–170 (1984).

*Primary Examiner*—Esther M. Kepplinger
*Attorney, Agent, or Firm*—Arnold, White & Durkee

[57] ABSTRACT

Hybridomas secreting monoclonal antibody having specificity for and cytolytic against *Trichomonas vaginalis* are provided. The cytolytic monoclonal antibodies specific for *T. vaginalis* are useful in detecting the presence of *T. vaginalis* among a general population of micro-organisms found in a biological sample. Detection of the *T. vaginalis* is evaluated by observing cell lysis of *T. vaginalis* after contacting the cultured micro-organisms with the cytolytic monoclonal antibody specific for *T. vaginalis*. Therapeutic uses of the monoclonal antibody as an immunological anti-microbial reagent for the treatment of *T. vaginalis* infection are also disclosed.

8 Claims, No Drawings

HYBRID CELL LINE PRODUCING MONOCLONAL ANTIBODY CYTOLYTIC TO *TRICHOMONAS VAGINALIS*

This application is a continuation in part application of copending U.S. patent application Ser. No. 544,473 filed Oct. 24, 1983.

BACKGROUND OF THE INVENTION

The present invention relates to monoclonal antibodies specific for *Trichomonas vaginalis*. More specifically, this invention relates to hybridomas which produce monoclonal antibodies specific for *T. vaginalis* antigenic determinants and which are cytolytic to this pathogenic microorganism. This invention relates to the use of monoclonal antibody for treatment of trichomoniasis.

Trichomoniasis is a chronic disease of the urogenital tract caused by *Trichomonas vaginalis*. It is the most common of all sexually transmitted diseases and is responsible for a significant economic and emotional burden among infected individuals in this country and the world. In women, trichomonal vaginitis is characterized by inflammation of vaginal epithelium, foul-smelling discharge, and tissue cytopathology. Most men are asymptomatic. Disease manifestations such as urethritis, prostatitis, balanoposthitis, and others, however, have been documented in infected men.

Current clinical diagnosis of trichomoniasis based on microscopic detection of the parasite is tedious, time consuming, highly inadequate, and expensive. These diagnosis limitations exacerbate already limited medical care in rural health clinics in our country and the world. Thus, basic research is necessary to address relevant issues such as development of sensitive, accurate assays for screening symptomatic as well as asymptomatic patients and perhaps monitoring disease progression. The development of potential vaccinogen and antibacterial candidates is equally important and necessary.

Further, the emergence of trichomoniasis as a major sexually transmitted disease has necessitated identification of the virulence factors associated with the surface of *T. vaginalis*. The use of conventional immunological methods has failed to identify specific virulence determinants or antigens.

It, therefore, is highly desirable to provide monoclonal antibody to *T. vaginalis* antigens. Such antibodies would be important in the differential diagnosis of trichomoniasis disease in humans, in the purification of specific immunogens for subsequent use as vaccines, and studying the structure and function of immunogenic components of virulent *T. vaginalis*.

While treatment of most women infected with *T. vaginalis* with metronidazole (Flagyl) or other imidazole drugs is highly efficacious, no treatment is provided for pregnant women. These drugs are known to cause cancer in laboratory animals and are teratogenic to the growing embryo and fetus. For this reason, alternative means for treatment are important and needed. Therefore, a monoclonal antibody which is cytolytic to intact live organisms would be important in abrogating existing disease in an untreated human subpopulation. Equally important would be the utility of such a reagent for emerging drug-resistant strains.

SUMMARY OF THE INVENTION

In accordance with the present invention, continuous hybridoma cell lines are established which elaborate and secrete highly specific and homogenous monoclonal anti-bodies to an antigen of *Trichomonas vaginalis*. Specifically, hybridoma cell lines are produced which secrete monoclonal antibodies having specificity for a *T. vaginalis* membrane glycoprotein antigen.

Of the three hybrid clones screened which exhibited monoclonal antibodies specific for and cytolytic to *T. vaginalis*, one hybrid line was deposited with the American Type Culture Collection in Rockville, Md.: C20A3, (HB 8379).

Further, the monoclonal antibodies according to this invention provide diagnostic and therapeutic reagents useful in the immunological detection and treatment of trichomoniasis infection.

DETAILED DESCRIPTION OF PREFERRED EMBODIMENTS

The following discussion is in terms of the preferred embodiments of this invention, which represent the best mode known to the Applicant at the time of this application.

I. GENERAL TECHNIQUES OF MONOCLONAL ANTIBODY PREPARATION

Antobodies are normally synthesized by lymphoid cells derived from B lymphocytes of bone marrow. The great diversity of antibody specificities is accomplished by immunoglobulin molecules having many structural features in common. Individual antibody molecules of heterogeneous binding specificity differ in their detailed amino acid sequences and even antibodies of the same specificity are usually a mixture of immunoglobulins having different amino acid sequences, although such sequences may be substantially homologous. The terms "antibody" and "immunoglobulin" are used interchangeably herein.

Individual lymphocytes produce immunoglobulin of a single amino acid sequence. Lymphocytes cannot be directly cultured to produce their specific antibody. However, Kohler, et al, *Nature* 256:495 (1975) demonstrated that a process of somatic cell fusion, specifically between a lymphocyte and a myeloma cell, could yield hybrid cells which grow in culture and produce a specific antibody. Myeloma cells are lymphocyte tumor cells which, depending upon the cell strain, frequently produce an antibody themselves, moreover some "non-producing" strains are known.

Several myeloma cell lines may be used for the production of fused cell hybrids, including P3/X63-Ag 8, P3/NSI/1-Ag 4-1, Sp2/10-Ag14 and S194/5.XXO.-BU.1. The P3/X63-Ag 8 and P3/NSI/1-Ag 4-1 cells lines have been described by Kohler and Milstein *Eur. J. Immunol.* 6: 511–519 (1976). Shulman et al. *Nature* 276: 269–270 (1978) developed the Sp2/O-Ag 14 myeloma line. The S194/5.XXO.BU.1 myeloma line was reported in an article by Trowbridge *J. Exp. Med.* 148: 313 (1979).

The hybrid resulting from somatic fusion of a lymphocyte and a myeloma cell is termed a "hybridoma" cell herein and in the art generally. In a typical fusion procedure, spleen lymphocytes from an animal immunized against a chosen antigen are fused with myeloma cells. The resulting hybridomas are then dispersed in a series of separate culture tubes or microtiter plate wells to screen for cultures producing a desired antibody. Positive cultures are further diluted to obtain colonies arising from a single cell (clones). The clones are again screened for production of the desired antibody. Antibody produced by a cloned hybridoma is termed "monoclonal" herein and in the art.

Monoclonal antibodies are highly specific, being directed against a single antigen only. Furthermore, in contrast to conventional antibody preparations which typically include different antibodies directed against different sets of determinants on the same antigen, monoclonal antibodies are directed only against a single determinant on the antigen. Monoclonal antibodies are useful to improve the selectivity and specificity of diagnostic and analytical assay methods using antigen-antibody binding. A second advantage of monoclonal antibodies is provided by the fact that they are synthesized in pure form by the hybridoma culture, uncontaminated by other immunoglobulins. Monoclonal antibodies may be prepared from supernatants of cultured hybridoma cells or from ascites induced by intraperitoneal inoculation of hybridoma cells into mice.

In accordance with the processes to develop the hybrid cell lines and monoclonal antibodies of this invention, test animals are stimulated for antibody production by different immunization regimens and using different antigen preparations of *Trichomonas vaginalis* pathogenic to humans as outlined below. For example, immunization of test animals was performed following subcutaneous inoculation of live organisms in the hind quarters of BALB/c mice. Applicant has directed the preferred embodiment to immunization of mice with a heterogeneous composition of parasite materials, thereby providing a complex array of antigen determinants. Although the mouse system has been employed as the antibody source of this invention, other antibody sources are available such as rabbits, rats, horses, and humans. Of course, the antibody source animals are not limited to those listed herein. Any animal which elicits antibody production after primed to an antigen is contemplated as an antibody source for the fusion process.

The route and schedule of immunization of the host animal is as described below. Mice were challenged subcutaneously with a booster inoculation approximately 25 days after the initial injection, and this procedure has been recently published (Alderete, *Brit. J. Vener. Dis.* 60:164, 1984). The kinetics of the IgG antibody response was monitored by a whole cell enzyme-linked immunosorbent assay. When maximal IgG levels were recorded approximately 14 days after the booster injection, mice were inoculated again. Three or four days after this last challenge, mice spleens were used for generation of hybridomas as described below. Otherwise, procedures are in keeping with established and conventional techniques for antibody stimulation and production.

After immunization, immune lymphoid cells are fused with myeloma, plasmacytoma, or hybridoma cells (hereinafter referred to collectively as myeloma cells) to generate a hybrid cell line which can be cultivated and subcultivated indefinitely, to produce large quantities of monoclonal antibodies.

For purpose of this invention, the immune lymphoid cels selected for fusion are lymphocytes and their normal differentiated progeny, taken either from lymph node tissue or spleen tissue from immunized animals. Applicant prefers to employ immune spleen cells, since they offer a more concentrated and convenient source of antibody producing cells with respect to the mouse system.

The myeloma cells provide the basis for continuous propagation of the fused hybrid. Myeloma cells are tumor cels derived from plasma cells which show preference for bone marrow. Plasmacytoma cells are neoplatic cells derived from plasma cells. In particular, Applicant prefers to use lymphocyte hybridoma cells which secrete no immunoglobulin. Lymphocyte hybridoma cells are cells generated by the fusion of myeloma or plasmacytoma cells with normal differentiated lymphoid cells. Myeloma, plasmacytoma, and hybridomas can be selected to be devoid of immunoglobulin synthesis.

The particular species of animal from which the myeloma and immunized antibody producing cells are derived are not critical, in that it is possible to fuse cells of one species with another. However, it is preferred that the source of immunized antibody producing cells and myeloma be from the same species.

Generally the fusion techniques employed are according to the procedures set out by Kohler et al, *Eur. J. Immunol.* 6:11-19 (1976) and Kennett et al, *Lymphocyte Hybridomas—Current Topics in Microbiology and Immunology* 81:77-91 (1978) Springer-Verlag, New York. Fusion is generally accomplished by centrifuging the myeloma cells with a suspension of antibody producing cells and growth medium to form a pellet.

The fused hybrids are next screened for antibody production specific for *T. vaginalis* surface antigens. The membrane-specific monoclonal antibodies obtained according to preferred examples include antibodies with individual specificity for the numerous antigenic components of the membrane, including lipids, glycoprotein and protein antigenic determinants.

The hybridomas which secrete antibody specific for *T. vaginalis* membrane antigens are cultured to establish a continuous cell line with stable genetic coding. These cell lines can be stored and preserved in any of a number of conventional ways, including freezing and storage under liquid nitrogen. Frozen cell lines can be revived and cultured indefinitely with resumed synthesis and secretion of monoclonal antibodies specific for *T. vaginalis* antigen. The secreted antibody is recovered from tissue culture supernatant by conventional precipitation, ion exchange, affinity chromatography, or the like. The recovered antibody can be freeze dried and stored under refrigeration for at least several weeks without significant loss of activity.

The following examples are offered to illustrate a particular embodiment of the invention but they are not intended to limit it.

II.

EXAMPLES OF MONOCLONAL ANTIBODY SPECIFIC FOR *T. VAGINALIS*

A. Preparation of Antigen

Strains used for preparing and assaying monoclonal antibodies include a long-term grown culture, strain RU 375 and NYH 286 obtained from Dr. Miklos Muller, Rockefeller University, New York and fresh isolate JHH obtained from Michael Spence, The Johns Hopkins University (Baltimore, Md.).

*Trichomonas vaginalis* was grown in a Diamond trypticase (BBL Microbiology Systems, Cockeysville, Md.)—yeast extract-maltose (TYM)-medium, pH 6.2, supplemented with 10% heat-inactivated horse serum (Kansas City Biologicals, Inc., Lenexa, Kans.). Organisms routinely grew to a density of $2.5 \times 10^6$ to $5 \times 10^6$ per ml as determined with an improved Neubauer counting chamber. Only motile parasites at logarithmic stage of growth were utilized.

Stock cultures of all *T. vaginalis* strains were stored in liquid nitrogen in TYM-serum medium containing 10% dimethylsulfoxide (DMOS). All strains remained virulent throughout these studies as evidenced by lesion development in mice after 9–12 days post-subcutaneous inoculation.

Antigen used for immunization a. For studies where spleen lymphocytes from animals challenged with live organisms were desired, the trichomonal strains NYH 286 and RU 375 were grown to logarithmic phase representing $1 \times 10^6$ organisms per ml. The parasites were then washed twice in sterile phosphate-buffered saline (PBS) and finally resuspended to a density of $5 \times 10^6$ per 0.5 ml volume in TYM-serum with 0.05% agar. A second injection was performed (as indicated in the next section) with organisms in TYM-serum medium followed by a third injection with *T. vaginalis* suspended in PBS.

b. Crude plasma membranes of *T. vaginalis* strain NYH 286 were generated from $2 \times 10^8$ cells. The organisms were washed three times in PBS followed by resuspending the organisms in PBS containing 10 mM $MgCl_2$ and 0.5 mg/ml concanavalin A. The organisms agglutinated and were washed twice further with PBS-10 mM $MgCl_2$. Pelleted trichomonads were resuspended in 10 ml of 1M glycerol and injected into 12 ml of 10 mM tris-hydrochloride buffer (tris-HCl), pH 7.5, containing 2 mM phenylmethyl-sulfonylfluoride (PMSF) and 1 mM $MgCl_2$. After a 10-minute incubation, the cells were homogenized further with a teflon pestle Dounce homogenizer (20 strokes) and cell lysis verified by examination of the cell preparation using darkfield and phase optics on a Zeiss IM30 microscope. The homogenate was then layered on a two-step gradient consisting of 8 ml of 0.5M mannitol over 5 ml of 0.58M sucrose. The gradient was centrifuged at $250 \times$ g for 30 minutes to form a pellet. The pellet represented crude membranes used for immunization protocols.

Electrophoretic analysis of crude membrane material confirmed to presence of immunogenic proteins and glycoproteins previously identified as residing on *T. vaginalis* membranes (Alderete, *Infect. Immun.* 40:284, 1983). Protein values were determined by the Bradford technique (Bradford, *Anal. Biochem.* 72:248, 1976).

B. Immunization Schedule for Hybridoma Production

Different immunization protocols were used depending on the antigen employed for generating immune spleen cells. Monoclonal antibodies illustrated in this embodiment are from three separate hybridization experiments, each representing the antigen described above. Spleen cells from two mice were used for each hybridization. Six to eight week old BALB/CJ female mice (Jackson Laboratories, Bar Harbor, Me.) were employed for these studies.

1. Live organisms

Mice were infected in the hind quarters by subcutaneous injection of 0.5 ml containing no less than $5 \times 10^6$ organisms per site. A second booster inoculation was performed at day 25 and a final challenge was given at day 39. Spleen cells were aseptically removed for use in hybridoma production from the immunized mice three days after the last inoculation with live organisms. This regimen allowed for the production of high-titered serum antibody levels as assayed by colarimetric (ELISA) and radioimmun precipitation-electrophoretic (RIP) techniques.

2. Crude membrane antigen

Each of two mice were given intraperitoneal injections with 1 ml of a 1:1 mixture of crude membrane (2 mg protein/ml) and Freund's complete adjuvant. Two booster inoculums also given intraperitoneally with identical protein levels in Freund's incomplete adjuvant at days 14 and 28 after the initial injection. Spleens from each of both mice were removed for use in hybridoma production from the immunized mice three days after the last injection of antigen.

C. Construction of Hybridomas

Hybridomas were produced by fusing spleen cell from the immunized mice with murine SP2/O-Ag14 hybridoma cells (SP2/O hereinafter) using a modification of the basic procedure of Oi and Herzenberg, *Immunoglobulin-Producing Hybrid Cell Lines*, In Selected Methods in Cellular Immunology, B. B. Mishell and S. M. Shiigi, eds., pp. 351–37, W. H. Freeman and Co., 1980, San Francisco. Suitable cell lines were obtained from Ed Hayes, Duke University and are as originally set forth by Schulman et al, *Nature* 276:269–270 (1978).

The SP2/O hybridoma cell line is a hybrid cell line derived from SP2/HGLK formed as a hybrid between a BALB/c spleen cell and the myeloma cell lines X63-Ag8. This cell line synthesizes no immunoglobulin chains, lacks the enzyme hypoxanthine guanine phosphoribosyl-transferase (HGPRT), is resistant to 8-azaguanine, and dies in the presence of Littlefield's hypoxanthine-aminopterinthymidine (HAT) selection medium. SP2/O cells were grown in Dulbecco's Modified Eagle's Medium (DMEM) (Microbiological Associates, Walkersville, Md.) supplemented with 15% (vol/vol) heat-inactivated fetal calf serum (Microbiological Associates), 2 mM L-glutamine, and 50 units/ml penicillin and 50 ug/ml streptomycin. SP2/O cells were grown in this medium containing 8-azaguanine (20 ug/ml) immediately prior to use in hybridization experiments to ensure that no HGPRT-positive revertants were present in the cell culture.

Spleens were removed aseptically from immunized mice and teaseds apart gently with forceps to prepare a single cell suspension in DMEM-1 mM Hepes buffer (Microbiological Associates). SP2/O cells were harvested in the logarithmic phase of growth and both cell types were collected by centrifugation at $270 \times$ g for 10 minutes at 8° C. and washed three times with DMEM. Total cell numbers were determined with a Neubauer Counting hemocytometer and viability was measured by trypan blue exclusion.

Approximately $10^8$ spleen cells were mixed together with SP2/O cells in a 50 ml conical tube at a ratio of 7 viable spleen cells per viable SP2/O cell and the resultant cell suspension was collected in a pellet by centrifugation at $270 \times$ g for 10 minutes. The supernatant medium was removed and the tube containing the cell pellet was placed in a 37° C. water bath for 1 minute. A 1.0 ml portion of a warm (37° C.) 50% (wt/vol) solution of polyethylene glycol (PEG 1000; ATCC) in DMEM per $1-2 \times 10^8$ spleen cells was added to the cell pellet with gentle stirring over a 1-minute period. The suspension was stirred an additional minute. Then, 1 ml(per $1-2 \times 10^8$ spleen cells) of DMEM was added over an additional 1-minute period and this step repeated once more. Finally, 7 ml (per $1-2 \times 10^8$ spleen cells) DMEM with 20% fetal bovine serum (tested for hybridoma growth, Microbiological Associates) was added over 2-3 minutes. The cells were then centrifuged at 400× g for 10 minutes and cells resuspended to 2-4×10$^6$ per ml in HY medium (Kennet et al, *Lymphocyte Hybridomas—Current Topics in Microbiology and Immunology*, Vol., 81, pp. 77-91 (1978) Springer-verlag, New York) and dispensed in 50 ul portions containing 2-4×10$^5$ cells into each well of 96-well plates (Costar Plastics, Vineland, N.J.), which were then incubated at 37° C. in a humidified incubator containing a 7% $CO_2$ atmosphere.

On day one, a 50 ul portion of a two-fold concentration of Littlefield's HAT selection medium was added to each well. An additional 50 ul portion of HAT was added to each well on day four.

The unfused SP2/O cells died in HAT within 24-48 hours. Cell growth in HAT medium is indicative of successful hybridization. Hybrid clones selected in HAT were usually observed by day six. After day six, all wells were fed (HT)-glycine medium, which comprises HY medium containing 1.6×10$^{-4}$M hypoxanthine, and 3×10$^{-6}$M glycine. Wells which contained growing clones were assayed to detect monoclonal antibodies directed at *T. vaginalis* surface antigens and cells where supernatants were positive for antibody toward parasites were transferred from these individual wells into a respective well of a 24-well tissue culture plate (Costar Plastics). Hybrid clones were maintained in HY medium without feeder layers and sequentially expanded to grow in T75 (750 mm$^2$ flasks; Costar) for freezing of cell lines in 90% Fetal bovine serum (Microbiological Associates)—10% DMSO (ATCC) in liquid nitrogen.

D. Characterization of Monoclonal Antibody

1. Analysis of Anti-*T. vaginalis* Membrane Antigen Activity in Hybridoma Supernatants Screening of hybrid clone culture supernatants for the presence of monoclonal antibodies directed against *T. vaginalis* membrane antigens was performed using an ELISA technique (Alderete, *Brit. J. Vener. Dis.* 60:164, 1984). Live trichomonas in logarithmic phase of growth were washed well in PBS and 50 ul representing 1.25×10$^5$ organisms were plated onto individual Immulon II strip wells (Dynatech, Alexandria, Va.). The cells were allowed to dry at 37° C. followed by fixation with 100% ethanol. Antigen-coated wells remained stable over a period of 6 months and were stored at 4° C. until use.

Antigen-coated wells were washed three times with pH 7.2 phosphate buffered saline (PBS). PBS (300 ul) containing 1% (wt/vol) bovine serum albumin (BSA) was incubated in each microtiter well for 1 hour at room temperature to saturate nonspecific protein binding sites in the plastic well. This solution was then removed by aspiration, the wells were washed three times with PBS, 100 ul of hybrid clone culture supernatant was added to the well and the microtiter plate was incubated at 37° C. for 120 minutes. Positive control wells contained mouse serum obtained from the same mouse whose spleen was employed for hybridization.

Supernatant fluid was then removed by aspiration, the microtiter wells washed three times with PBS, and alkaline phosphatase-conjugated goat antimouse immunoglobulins (Cappel Laboratories, Cochranville, Pa.), prepared by the method of Voller et al. Bull. WHO 53:55-65, 1976), and diluted 1/500 in PBS, was then added to a final volume of 200 ul in each microtiter well. The microtiter plates were incubated at 37° C. for one hour after which the conjugated antisera was removed by aspiration, the wells washed three times with PBS, and 300 ul of enzyme subtrate [p-nitrophenyl phosphate (Sigma); 1 mg/ml in 10% (vol/vol) diethanolamine buffer (pH 9.8) containing 1 mM $MgCl_2$] was added to each well. Thirty minutes later, the absorbance of the solution in each well was determined spectrophotometrically at 405 nm using a Dynatech Micro-ELISA reader (Dynatech, Alexandria, Md.). Microtiter wells in which the absorbance was at least two-fold greater than background levels of absorbance obtained with antigen-free control wells were scored as positive for the presence of antibodies directed against *T. vaginalis* membrane antigens.

Of approximately 500 hybrid clones screened, 3 hybrids demonstrated cytolytic antibody reactive against *T. vaginalis* glycoprotein antigen determinants. These monoclonals are designated C20A3, 375-1, and DM-155. Clone C20A3 was deposited with the American Type Culture Collection, Rockville, Md. and accorded the respective deposit numbers HB8379.

2. Isotypic Analysis

Cultures positive for antibodies against *T. vaginalis* were next tested to identify the mouse antibody isotype, using standard immunological assays employing rabbit anti-mouse subclass antibody reagents and peroxidase-conjugated affinity purified goat anti-rabbit IgG2a (H&L) for use in standard ELISA (Mouse immunoglobulin subtype identification kit, Boehringer Mannheim Biochemicals, Indianapolis, Ind.). All monoclonal antibodies were of the IgG subclass.

3. Analysis of Anti-*T. vaginalis* Membrane Protein Activity in Hybridoma Supernatants Culture supernatant fluids from hybrid clones which scored positive in the ELISA test were assayed by a radio-immunoprecipitation method (Alderete, *Infect. Immun.* 39:1041, 1983 and Alderete, *Infect. Immun.* 40:284, 1983) for the presence of monoclonal antibodies directed against trichomonal membrane proteins.

Membrane proteins of *T. vaginalis* were radioiodinated by a recently published method (Alderete, *Infect. Immun.* 40:284, 1983). Radioiodinated cells were extensively washed with PBS and pelleted organisms resuspended with 200 ul of NET (150 mM NaCl, EDTA, 50 mM Tris-hydrochloride, pH 7.2) buffer containing 1mM PMSF (Sigma) and placed in a 37° C. water bath for 10 minutes. Twenty-five microtiters of 10% Zwitterionic 3-12 (Z3-12) detergent (Calbiochem-Behring Corp., La Jolla, Calif.) was then added, and the mixture was gently homogenized until the trichomonads were solubilized. An additional 20 ul of NET buffer was added, and the detergent extract was centrifuged over a 5% sucrose bed for 30 minutes at 100,000× g with a Beckman SW50.1 rotor. Greater than 80% of the initial radioactivity was routinely recovered in the supernatant.

Before mixing with antibody, the Z3-12 extract was preadsorbed with 100 ul of 10% (vol/vol) Formalin-fixed, protein A-bearing *S. aureus* to remove nonspecific binding proteins. Then 100 ul of the adsorbed solubilized trichomonal proteins was mixed with 50 ul of hybridoma supernatant and incubated overnight at 4° C. Finally, 100 ul of 10% (vol/vol) fixed protein A-bearing *S. aureus* was added, and incubation was continued at room temperature for a further 2 hours. The protein A-bearing *S. aureus*-adsorbed immune complexes were then sedimented at 10,000× g for 4 minutes and washed three times in NET-0.5% Z3-12 buffer. Radiolabeled antigen-antibody complexes were then solubilized in electrophoresis dissolving buffer. The samples were suspended and boiled for three minutes, and protein A-bearing *S. aureus* cells were removed by centrifugation. The supernatants containing parasite protein antigens were finally loaded on SDS-polyacrylamide slab gels. Electrophoresis was performed as described (Alderete, *Infect. Immun.* 39:1041, 1983), and gels were fixed and processed for fluorography. The protein A-bearing *S. aureus* cells were sequentially washed in 0.5% Z3-12 and 0.05% Z3-12 in NET buffer just before use. The formaldehyde-fixed protein A-bearing *S. aureus* organisms employed in these studies were grown and prepared as described elsewhere (Alderete and Baseman, *Infect. Immun.* 26:1048, 1979). Equally important was immunoprecipitation of trichomonal proteins biosynthesized and radiolabeled with [$^{35}$S]-methionine with molecular weights identical to those obtained with radioiodinated organisms.

A total of three monoclonal antibodies from four hybridization experiments using different antigens were shown to be directed at a *T. vaginalis* glycoprotein which is highly immunogenic in mice infected with live parasites and patients with trichomoniasis. The membrane glycoprotein possesses a molecular weight of approximately 230,000 daltons (230Kd) when the different monoclonals were tested against the commonly used strain NYU 286. Other molecular weights were noted for some strains.

4. Analysis of Monoclonal Antibodies with Cell Surface Exposed Proteins

In addition to analysis of the surface location of the parasite antigen by a whole cell ELISA and radio immunoprecipitation procedures, supernatants of hybrid cell lines were tested by indirect immunofluorescence using live strain NYH 286 as test *T. vaginalis* organisms. All monoclonals resulted in strong fluorescence of the organisms. Thus, the epitopes for this antigen are readily exposed on the parasite surface.

5. Monoclonal Antibody Reactivity to a Protein Epitope and Not a Sugar Epitope

The reaction of the antibodies to the protein component of the glycoprotein molecules was established using a modification of the ELISA procedure stated earlier (Alderete, *Brit. J. Vener. Dis.* 60:164, 1984) and indirect immunofluorescence as just described. Briefly, *T. vaginalis* fixed on individual wells of microtiter plates were treated with increasing levels of periodic acid ranging from 0.001 mM to 100 mM for 15 to 30 min at 37° C. Periodate is known to break vicinyl hydroxyl groups in carbohydrate structures and conditions used are known to destroy sugars on all surfaces (Ofek et al., *Nature* (London) 265:623, 1977). Following treatment with periodate, the respective monoclonals are reacted with the treated and untreated control parasites, and the ELISA performed as before. In all cases the ELISA reactivity was positive indicating the epitope for antibody binding on the protein moiety. Strong fluorescence was also noted on periodate-treated trichomonads.

6. Strain Distribution of the Antigenic Determinant

It was of interest to determine if the antigenic determinant recognized by one of the key monoclonal antibodies was unique to the immunizing *T. vaginalis* strain or whether this antigenic determinant might be found in all other pathogenic human trichomonal strains. Accordingly, nine different clinical isolates of *T. vaginalis* (strains NYH 286, NYH 272, ATCC 30001, ATCC 30236 (JH31A), JHHZH, JHHR, JHHR, JHHEL, and JHHW) collected over a two-year period were examined for the presence of the antigenic determinat recognized by monoclonal antibodies.

One ug ascites of C20A3 monoclonal were added to microtiter plate wells (Voller, et al, Manual Clinical Immunol. 1976), and to individual wells was added 50 ul of *T. vaginalis* detergent extract obtained from a 1 ml final volume. After a 60-min incubation, the wells were washed with PBS followed by sequential addition to wells of rabbit antisera to *T. vaginalis* (strain NYH 286) and goat anti-rabbit Ig (alkaline-phosphatase conjugated).

All monoclonal antibodies detected all strains to the same extent as the homologous strain employed as the immunization agent, strain 286. Importantly, strains 286 and JH31A were cultivated in vitro for several years and thus represented long-term grown cultures while the other strains were fresh isolates grown for no longer than 3–4 days in Applicant's laboratory prior to testing.

7. Cytolytic Activity by Monoclonal Antibodies

Monoclonal antibodies were all, of the IgG subclass and were purified by protein A-Sepharose affinity chromatography. Immunoglobulin was eluted with IM AcOH in PBS, dialyzed against two changes of distilled water, concentrated by Amicon ultrafiltration, and dialyzed against PBS. These monoclonals in physiological saline were then employed for studies mentioned below.

A 0.1 ml sample of $2 \times 10^6$ organisms washed twice with PBS was mixed with an equal volume of purified monoclonal IgG or control IgG of the same subclass but unreactive with *T. vaginalis* (i.e. antimycoplasma IgG antibody). After 20 min at 37° C. with gentle shaking, the parasites were washed twice with PBS and resuspended to a 1 ml final volume in PBS. Numbers were determined and a quantitative assessment of lysis determined under these conditions. Up to 85% lysis wa achieved using strain NYH 286 with monoclonal C20A3. Lysis was also evident using the DM-155 and 375-1 monoclonals under the same conditions.

The cytolytic potential of the respective monoclonals was also evaluated by demonstrating the release of ($^3$H)-thymidine-labeled DNA of live trichomonads after incubation of *T. vaginalis* organisms with antibody under a variety of conditions. The data obtained from these type of experiments correlated with those mentioned above involving microscopic enumeration and quantitation of killed organisms.

E. Utility

The hybridoma cell lines and the monoclonal antibodies produced therefrom described in this application are useful in the purification and characterization of specific antigenic and immunogenic components presented by *Trichomonas vaginalis* organisms. Moreover, the monoclonal antibodies produced from a given hybridoma line are homogeneous in antigenic recognition and thereby are useful for subsequent affinity chromatography-based purification of trichomonal membrane antigens.

Furthermore, the availability of different monoclonal antibodies directed against one or more antigenic determinants of the same outer membrane antigen of *T. vaginalis* is useful in studying the structure and function of membrane components. Similarly, these same monoclonal antibodies are valuable in the idiotypic analysis of antibody response to cell surface structure of a pathogenic micro-organism.

Ultimately, the availability of monoclonal antibodies directed against selected *T. vaginalis* membrane antigens, in particular cell surface-exposed membrane proteins, will facilitate studies on the vaccinogenic potential of these proteins.

Monoclonal antibodies specific to and cytotoxic for *T. vaginalis* can be used clinically for the prevention or treatment of trichomoniasis. For example, monoclonal antibodies specific for surface antigens of *T. vaginalis* can be used clinically for the prevention and/or treatment of trichomonal disease in animals, including human adults. The mode of administration of these monoclonal antibodies is preferably oral. The monoclonal antibodies may be suspended or dissolved in any of several suitable liquid vehicles and delivered to the host by one or several oral means. The ascites fluid of the animal or the in vitro culture medium in which the antibody-producing clones were propagated are pharmaceutically acceptable liquid carriers for animals and may be used directly without purification or concentration though a clarification step may be desirable. In some instances and particularly where human treatment is involved, purification may be desired or required pursuant to governmental regulation.

In humans, the monoclonal antibody compositions are preferably administered in capsular form, though any compatible carrier may be used.

The *T. vaginalis* specific monoclonal antibodies are also useful for medical research purposes. For instance, these monoclonal antibodies can be used diagnostically to detect with great accuracy the presence of *T. vaginalis* strains among a general population of bacteria.

The foregoing description of the invention has been directed to particular embodiments for purposes of explanation and illustration. It will be apparent, however, to those skilled in the art that many modifications and changes in the processes of preparing and implementing the described embodiments may be made without departing from the essence of the invention.

For example, it is contemplated that hybridoma cell lines may be developed using human myeloma cells and human lymphocytes primed to membrane antigens of *T. vaginalis*.

In another example, monoclonal antibodies can be developed which are specific for individual *T. vaginalis* strains other than strain 286 used in these hybridization experiment. Also, hybridoma cells can be constructed from the differentiated lymphoid cells of mice immunized by alternate routes and methods. Similarly, other mouse strains can be used to produce hybridoma cells elaborating similar sets of monoclonal antibodies suitable to the purposes described herein. These and other modifications and uses of the depicted embodiment, as well as other embodiments of the invention, will be apparent to those skilled in the art. It is Applicant's intention in the following claims to cover all equivalent modifications and variations as fall within the scope of the invention.

What is claimed is:

1. A continuous cell line which produces monoclonal antibodies against a membrane glycoprotein antigen of *Trichomonas vaginalis* and said antibodies being cytolytic to *Trichomonas vaginalis* organisms, comprising a hybridoma formed by fusing a cell capable of producing antibodies against *Trichomonas vaginalis* antigen with a myeloma cell, and said hybridoma producing monoclonal antibody specific to and cytolytic against *Trichomonas vaginalis* organisms and specific to the same glycoprotein as the monoclonal antibody produced by the hybridoma ATCC HB 8379.

2. The cell line of claim 1 wherein the membrane glycoprotein antigen has an approximate molecular weight of 230,000 daltons as measured by SDS-polyacrylamide gel electrophoresis.

3. The cell line of claim 1 which is a clone of ATCC deposit HB8379.

4. A composition consisting essentially of monoclonal antibody specific for and cytolytic against *Trichomonas vaginalis* and specific to the same membrane glycoprotein as the monoclonal antibody produced by the hybridoma ATCC HB 8379.

5. The composition of claim 4 wherein the monoclonal antibody is specific for a 230,000 dalton, membrane glycoprotein antigen of *T. vaginalis*.

6. The composition of claim 4 wherein the monoclonal antibody is a product from hybridoma clone ATCC deposit HP8379.

7. A method of detecting *Trichomonas vaginalis* among a population of micro-organisms in a biological sample comprising:
  culturing the micro-organisms found in the biological sample;
  contacting the cultured micro-organisms with monoclonal antibody specific for and cytolytic against *T. vaginalis* and specific to the same membrane glycoprotein as the monoclonal antibody produced by the hybridoma ATCC HB 8379; and
  observing cell lysis activity, which cell lysis is indicative of the presence of *T. vaginalis*.

8. The method of claim 7 wherein the cytolytic monoclonal antibody is a product from hybridoma clone ATCC deposit HB8379.

* * * * *